United States Patent [19]
Ruget

[11] 3,946,593
[45] Mar. 30, 1976

[54] MACHINE FOR TESTING BEARING GREASE

[75] Inventor: Gabriel Ruget, Saint-Etienne, France

[73] Assignee: Creusot-Loire, Paris, France

[22] Filed: June 10, 1974

[21] Appl. No.: 477,984

[30] Foreign Application Priority Data
June 22, 1973 France .................. 73.22900

[52] U.S. Cl. .................................. 73/10
[51] Int. Cl.² ............................ G01N 19/02
[58] Field of Search .......... 73/10, 9; 188/267

[56] References Cited
UNITED STATES PATENTS

| | | | |
|---|---|---|---|
| 2,685,947 | 8/1954 | Votrian | 188/267 |
| 2,883,855 | 4/1959 | Spengler et al. | 73/10 |
| 3,353,398 | 11/1967 | Lohmar et al. | 73/10 |

Primary Examiner—Richard E. Aegerter
Assistant Examiner—Willis Little
Attorney, Agent, or Firm—Cameron, Kerkam, Sutton, Stowell & Stowell

[57] ABSTRACT

A machine for testing bearing grease in which a shaft is supported in two bearings the outer race of each of which is set in a housing for the grease to be tested and breaking means for the shaft which will cause the bearings to heat.

14 Claims, 5 Drawing Figures

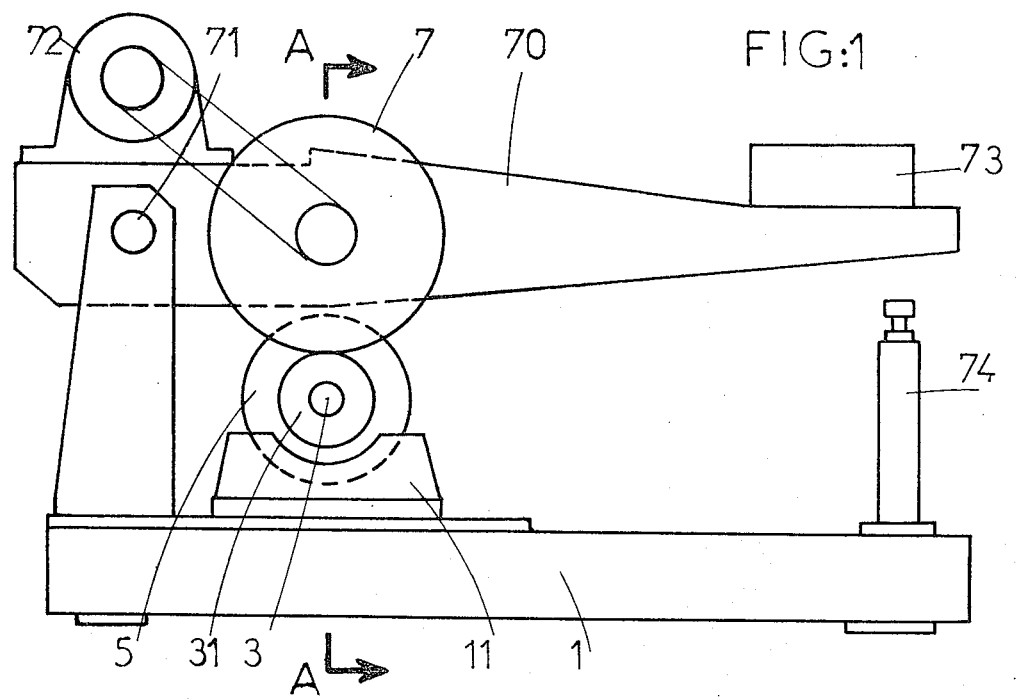
FIG:1
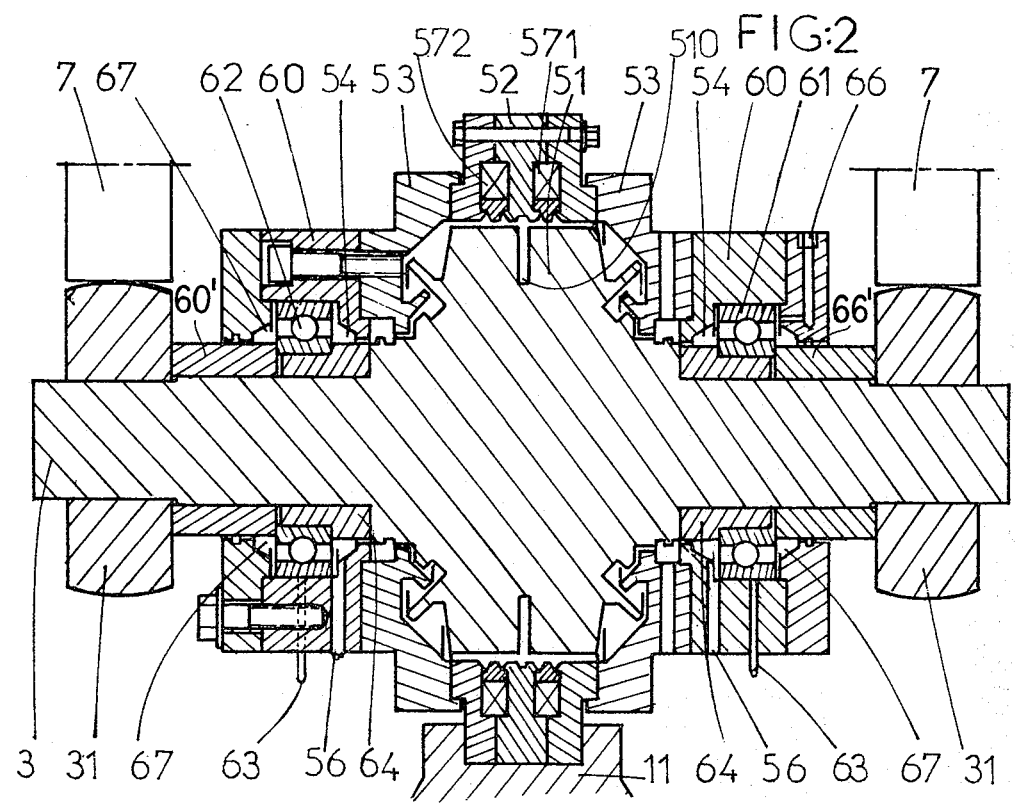
FIG:2

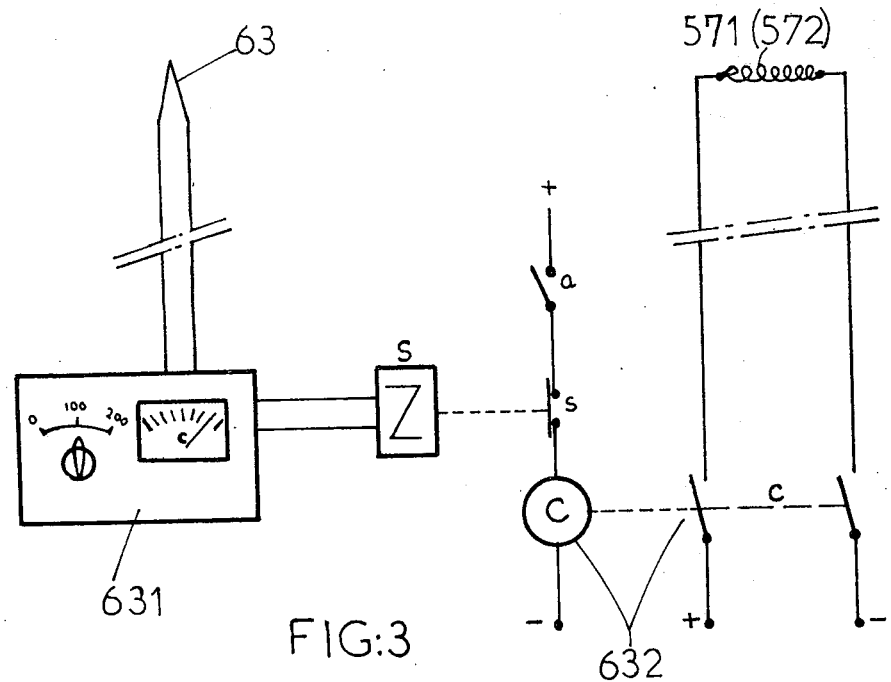
FIG:3
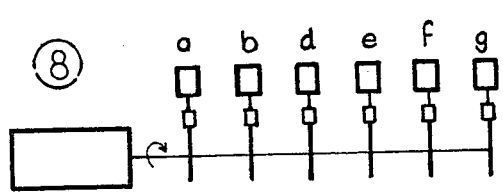
FIG:4a
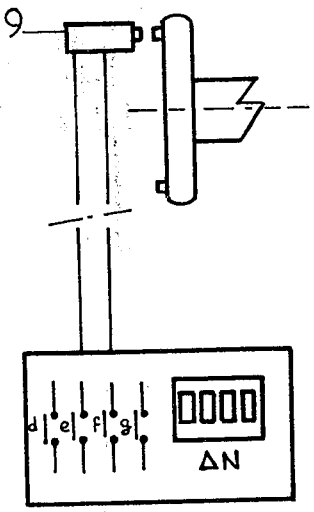
FIG:4b

MACHINE FOR TESTING BEARING GREASE

The invention relates to bearing-grease testing machines.

Various methods exist for testing the qualities of bearing-greases, generally by observing their behaviour in test bearings which may possibly be loaded and heated.

For doing this there exist numerous types of machine in which the testing of the grease is effected on one or two identical bearings filled with the grease to be tested, the outer race being integral with a frame and the inner race being driven in rotation by a shaft.

These machines enable study of either the rheological behaviour of the grease (due to shearing) or its endurance in time. Certain of them enable the frictional torque of the bearings to be determined by various methods (intensity induced in the motor, for example) with all the inaccuracies which that implies, owing particularly to the presence of other bearings in the motor or in plummer blocks carrying the loads.

In addition, in the majority of existing machines the means of heating the bearings generally consist of an enclosure heated by electrical resistors, in which are placed the bearings containing the grease to be tested.

This method of heating does not reproduce the most severe conditions of raising of temperature of a bearing in service for which the inner race is brought to a temperature distinctly higher than that of the outer race, which imposes upon the grease a more severe lamination. In addition it does not enable very accurate control of the bearing temperature.

In accordance with the invention there is provided a machine for testing greases on bearings, comprising a frame, a shaft, a means of driving the shaft in rotation, two bearings spaced apart, each comprising an inner race fixed to the shaft and an outer cage rigidly locked to a housing containing the grease to be tested, seals interposed between the shaft and the bearing housings, and a means of heating the bearings, which comprises means for braking the shaft, including an inner rotor fast with the shaft between the two bearings and a stator locked rotationally with respect to the frame, upon which are mounted on opposite sides of the rotor two cheeks each bearing the housing of one of the bearings.

In a preferred form of the invention for the control of the temperature the member for braking the shaft is an electromagnetic powder coupling.

Thus it may be seen that in the machine in accordance with the invention the heat is produced not by electrical resistors but by dissipation of the braking power in the form of heat, this heat thus being propagated partially through the cheeks of the brake up to the housings receiving the outer race of the bearings containing the grease to be tested, and preponderantly, from the construction, through the rotor shaft up to the inner race of these bearings, where the temperature is thus always higher than that of the outer race.

Furthermore the machine, particularly in its preferred embodiment, which will now be described by way of example, presents other advantages which will become apparent in the course of the description wich follows, and in which reference is made to the accompanying drawings, in which:

FIG. 1 is a diagrammatic view of the whole of one embodiment of the invention,

FIG. 2 is a partial section along A—A in FIG. 1,

FIG. 3 is a diagram of the bearing temperature regulation, and

FIG. 4 represents an example of automatism for the measurement of the deceleration of the rotating portion.

The machine represented in FIG. 1 comprises a frame 1 supporting a cradle 11 on to which is fixed an electromagnetic powder brake 5 represented in section in FIG. 2. The brake 5 comprises a stator 52 (FIG. 2) fixed rotationally by the cradle 11, and a shaft 3 which carries the inner races of two test bearings 61 and 62 located on opposite sides of the rotor 51 of the electromagnetic brake, the outer races of which are fast with bearing housings 60 mounted on two cheeks 53 of the stator 52. Seals 60' and 66' are interposed between the shaft 3 and housing 60. The rotor 51 can be an integral part of the shaft 3 as shown in FIG. 2 or constitute an independent part rigidly locked to the shaft 3.

The shaft 3 carries at its ends two domed-rim receiver-rollers 31 fixed symmetrically with respect to the equatorial plane of the rotor, upon which bear two cylindrical-rim rollers 7.

The shafts of the two cylindrical rollers 7 are each carried by a beam 70 (FIG. 1) hinged to the frame about an axis 71. One of the beams carries a motor 72 driving the shaft of one of the rollers 7 by means, for example, of a belt, the roller in turn driving by friction the corresponding roller 31 and the rotor. There is provided in addition means of loading the bearings. For this purpose each beam 70 carries overhung beyond the rollers 7 a load 73 the value of which may be adjusted according to the type of test. The electromagnetic brake 5 contains iron powder distributed in the gap separating the rotor 51 from the stator 52, the latter forming about the rotor a polar mass inside which are located two exciter coils 571 and 572. When current flows through these coils it creates a radial magnetic field in the gap which coagulates the iron powder in a manner increasing as a function of its intensity. The torque which tends to brake the rotor 51 is thus directly proportional to the current and for a given speed of the shaft 3 the power which results from it is dissipated in the form of heat being propagated on the one hand through the cheeks 53 and on the other hand and preponderantly through the rotor 51 and the shaft 3 towards the bearings filled with grease to be tested.

As may be seen from FIG. 2 independent regulation of the temperature of each bearing 61 and 62 is obtained by means of two exciter coils 571 and 572 located symmetrically with respect to the equatorial plane of the stator 52. In addition a deep narrow throat 510 may advantageously be arranged in the equatorial plane of the rotor 51. The thermal flow resulting from the excitation of each coil 571 (572) is thus channelled preponderantly towards the nearer bearing 61 (62). The temperature of one of the bearings can thus be substantially modified with respect to that of the other by acting upon the intensity of feed to the corresponding coil.

The temperature of each of the bearings is measured by means of thermocouples 63 applied, for example, to their outer races. FIG. 3 gives by way of example a diagram for regulation of the excitation intensity. Each thermocouple 63 is connected to a temperature programmer 631 upon which there might be displayed either a constant set temperature or a uniformly increasing temperature or any other law of variation of temperature with time. When the temperature of the bearing transmitted by the thermocouple reaches the required set value a relay 632 cuts off the feed to the corresponding exciter coil. The brake thereby cools and as soon as its temperature has dropped by, for example, 2°C the relay restores the current to the coil and so on.

The testing machine enables different types of test to be made. In particular the employment of an electromagnetic powder brake enables the temperature at the bearings to be controlled with accuracy and its regulation ensured.

Keeping at a fixed temperature for several hours can also be obtained in order to perform tests of the endurance of grease in industrial operation. Any cycle whatever can also be effected by controlling the time to rise of temperature and then the time of keeping at a fixed temperature.

There can likewise be carried out a continuous rise in temperature until the grease flling the bearing changes and flows into the circular recesses 54 arranged in the cheeks 53, then falls by gravity towards the outside thanks to ducts 56 provided for this purpose at the lowest point. The grease thus falls in the form of drops which can be recovered, for example, on a blotting paper passing by at known speed.

By noting the temperature starting from which the grease escapes through the aperture 56 the dynamic drop-point of a grease can be determined with accuracy.

Besides the possibility of obtaining at the bearings a given temperature and a given load the machine in accordance with the invention enables the drag torque of the test bearings alone to be determined.

For this purpose jacks 74 located under the overhung ends of the beams 70 enables the latter to be raised as required and thus the receiver rollers 31 to be freed in order to record the deceleration of the rotating portion supported solely by the bearings filled with the grease to be tested.

An automatism comprising a cam-programmer 8, represented diagrammatically in FIGS 4a and 4b by way of example, performs at regular intervals of time the following operations:

it cuts off the feed to the brake coils (contact $a$),
  it lifts the beams (contact $b$),
  immediately afterwards it counts by a known system such as a pulse detector 9 (FIG. 4b) the number of revolutions of the shaft during a very short time $t_1$ and stores them (contact $d$),
  at the end of a short period $t_2$ (contact $e$) it again counts the number of revolutions during the same time $t_1$ and subtracts it from the previous count, then displays this drop in speed or passes it to a contact $f$,
  to finish off, a contact $g$ returns everything to zero.

The development in the time of this fall in speed is directly connected with the state of the grease filling the bearings.

In addition, knowing the inertia of the rotating parts, it is possible to determine the drag torque of the bearings at mean speed during the interval of time. This interval being short, the mean speed is substantially that prior to the measurement.

It will be observed further that the layout represented in FIG. 2 enables easy replacement of the bearings. Actually a sleeve 64 is provided for each bearing in order to avoid impairing the shaft during successive dismantlings and reassemblies and also in order to enable the employment of bearings of diameters by employing a range of suitable sleeves. The receiver-rollers 31 are themselves fixed at each end by known means so as to be easily dismantlable. Moreover an aperture 66 is arranged in each housing 60 in order to enable either renewal of the grease which is distributed in the circular recess 67 or to introduce into the grease to be tested in a mist or drop by drop, plain water or water charged with various impurities such as salt, in order to study the behaviour of the greases in different media.

Finally, the stator 52 of the brake is fixed as indicated on a cradle 11 which locks it rotationally.

This cradle may be connected to the frame 1 by means of a suitable device not shown, enabling there to be imposed upon the stator vibrations perpendicular to the axis of rotation in the horizontal plane, of variable amplitude and frequency, which will be reflected on to the test bearings.

It may be seen that the machine enables a large number of tests to be performed. The employment of an electromagnetic powder brake enables the temperature to which the bearings are brought to be controlled with accuracy and the bearings to be subjected to an industrial operation which is hard upon the grease because the temperature of the inner race is higher than that of the outer race. The employment of beams enables any kind of load to be applied to the bearings, and by lifting them, to check frequently their natural drag torque by measuring the deceleration of the rotating portion. The perfect symmetry of this test-bench can enable two tests to be performed simultaneously, for example, the determination of the dynamic drop-point with higher accuracy, each bearing being able to serve as a check upon the other, or to try two different greases at the same time. Further, the possibility of adjusting the temperature of each bearing and loading each of them differently enables testing, for example, of the same grease under different operating conditions.

Of course the invention is not limited to the details of execution which have been described, but it encompasses on the contrary any variants and particularly those which would differ from it only by the use of equivalent means.

Thus the member for braking the shaft might be any brake the torque of which can be easily subordinated to the temperature of the bearings, for example, a Foucault-current brake.

Again, the symmetry of the machine might be still further increased by driving the two rollers 7 by means of two synchronous motors. Furthermore the means of driving in rotation the shaft carrying the rollers might also be composed, respecting the symmetry of the machine, by two motors located on the end of the shaft, and each motor could be mounted on a cradle slidable parallel with the axis of the shaft and connected to the shaft by a disconnectable coupling. Thus the shaft 3 could still be disconnected instantaneoulsy while running, in order to be able to record the deceleration of the rotating portion and deduce from it the bearing drag torque. In this case the application of loads to the bearings would be effected by the adding of known weight-discs at each end of the shaft 3.

What is claimed is:

1. A machine for testing greases on bearings, comprising a frame, a shaft, means mounted on said frame for rotating the shaft, two spaced housings containing the grease to be tested, two spaced bearings, each bearing comprising an inner race fixed to the shaft and an outer cage rigidly locked to one of said housings, seals interposed between the shaft and said housings, and means for braking and for heating the bearings including an inner rotor secured to the shaft between the two bearings, a stator locked rotationally with respect to the frame, and a cheek mounted on said stator on each side of the rotor each cheek supporting one of said housings of one.

2. A grease testing machine as in claim 1, wherein the means for braking the shaft is an electromagnetic brake and means for regulating the temperature of the bearings by control of the intensity of the excitation current of the brake.

3. A grease testing machine as in claim 2, wherein the braking means is an electromagnetic powder coupling.

4. A grease testing machine as in claim 3, wherein the powder coupling includes two coils mounted in the stator symmetrical with respect to the equatorial plane of the rotor.

5. A grease testing machine as in claim 4, including a means for regulating the temperature of each bearing by control of the intensity of the excitation current in the coil adjacent the bearing.

6. A grease testing machine as in claim 4, including a narrow deep throat in the equatorial plane of the rotor.

7. A grease testing machine as in claim 1, including a circular recess in each of said housings for receiving the grease and a duct at the bottom of each recess for exhaust of melted grease towards the outside.

8. A grease testing machine as in claim 1, including an aperture in each of said housings for supplying the grease to be tested a circular recess in each of said housings for distribution of the grease in said housings, said aperture opening into said circular recess.

9. A grease testing machine as in claim 1, including means for rapid disconnection of the means for rotating the shaft from the shaft.

10. A grease testing machine as in claim 9, including automatic means driven by the shaft and at regular intervals of time:

terminating the actuation of the brake, disconnecting the shaft from the means for rotating the shaft, recording in respect of the freely rotating rotor during a given short period $t_1$ the number of revolutions of the shaft, then at the end of an interval of time $t_2$ recording during the same period $t_1$ the number of revolutions of the shaft, and recording the difference between the two numbers of revolutions and therefore the drag torque of the two bearings at the average speed during the interval of time $t_2$.

11. A grease testing machine as in claim 1, the means for rotating the shaft including at least one driving roller, a receiver roller rigidly locked to the shaft and frictionally engaging the driving roller, the driving roller being mounted on a driving roller shaft, a motor rotating the shaft and a beam hinged on the frame supporting the motor and the driving roller shaft.

12. A grease testing machine as in claim 11, the beam havng a part extending beyond the roller away from the beam hinge and a load on the part.

13. A grease testing machine as in claim 11, including two driving rollers for driving two receiver rollers on the shaft symmetrically with respect to the median plane of the rotor, each driving roller being mounted on a beam and driven by a motor mounted on the beam.

14. A grease testing machine as in claim 9 the means for rapid disconnection including means for raising the beam.

* * * * *